(12) United States Patent
Whitehurst et al.

(10) Patent No.: US 7,769,461 B2
(45) Date of Patent: Aug. 3, 2010

(54) SKULL-MOUNTED ELECTRICAL STIMULATION SYSTEM AND METHOD FOR TREATING PATIENTS

(75) Inventors: Todd K. Whitehurst, Santa Clarita, CA (US); Rafael Carbunaru, Studio City, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1062 days.

(21) Appl. No.: 10/585,233

(22) PCT Filed: Dec. 17, 2004

(86) PCT No.: PCT/US2004/042711

§ 371 (c)(1),
(2), (4) Date: Jun. 30, 2006

(87) PCT Pub. No.: WO2005/062829

PCT Pub. Date: Jul. 14, 2005

(65) Prior Publication Data

US 2006/0293723 A1 Dec. 28, 2006

(51) Int. Cl.
*A61N 1/00* (2006.01)
(52) U.S. Cl. .......................................... 607/45; 607/63
(58) Field of Classification Search .............. 607/1–3, 607/6–8, 30–32, 44, 45, 46, 58, 59, 60, 63, 607/115, 116, 118, 126–132; 600/26
See application file for complete search history.

(56) References Cited

U.S. PATENT DOCUMENTS

| 3,646,940 A | 3/1972 | Timm |
| 3,760,984 A | 9/1973 | Theeuwes |
| 3,845,770 A | 11/1974 | Theeuwes et al. |
| 3,882,285 A | 5/1975 | Nunley et al. |
| 3,916,899 A | 11/1975 | Theeuwes et al. |
| 3,923,426 A | 12/1975 | Theeuwes |
| 3,987,790 A | 10/1976 | Eckenhoff et al. |
| 3,995,631 A | 12/1976 | Higuchi et al. |
| 4,016,880 A | 4/1977 | Theeuwes et al. |
| 4,036,228 A | 7/1977 | Theeuwes |
| 4,111,202 A | 9/1978 | Theeuwes |
| 4,111,203 A | 9/1978 | Theeuwes |

(Continued)

FOREIGN PATENT DOCUMENTS

EP        0999839 B1    6/2004

(Continued)

*Primary Examiner*—Mark W Bockelman
*Assistant Examiner*—Elizabeth K So
(74) *Attorney, Agent, or Firm*—Vista IP Law Group LLP

(57) ABSTRACT

A system and method for applying electrical stimulation or drug infusion to nervous tissue of a patient to treat epilepsy, movement disorders, and other indications uses at least one implantable system control unit (SCU) (110), including an implantable signal/pulse generator (IPG) and one or more electrodes (152, 152'). The IPG is implanted in the mastoid area (143) of the skull (140) and communicates with at least one external appliance (230), such as a Behind-the-Ear (BTE) unit (100). In a preferred embodiment, the system is capable of open- and closed-loop operation. In closed-loop operation, at least one SCU includes a sensor, and the sensed condition is used to adjust stimulation parameters.

14 Claims, 10 Drawing Sheets

U.S. PATENT DOCUMENTS

| | | | |
|---|---|---|---|
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,338,945 A | 7/1982 | Kosugi et al. | |
| 4,360,019 A | 11/1982 | Portner et al. | |
| 4,431,001 A | 2/1984 | Hakansson et al. | |
| 4,487,603 A | 12/1984 | Harris | |
| 4,495,917 A | 1/1985 | Byers | |
| 4,537,195 A | 8/1985 | McDonnell | |
| 4,612,934 A | 9/1986 | Borkan | |
| 4,627,438 A | 12/1986 | Liss et al. | |
| 4,627,850 A | 12/1986 | Deters et al. | |
| 4,692,147 A | 9/1987 | Duggan | |
| 4,702,254 A | 10/1987 | Zabara | |
| 4,725,852 A | 2/1988 | Gamblin et al. | |
| 4,856,526 A | 8/1989 | Liss et al. | |
| 4,865,845 A | 9/1989 | Eckenhoff et al. | |
| 4,867,164 A | 9/1989 | Zabara | |
| 5,057,318 A | 10/1991 | Magruder et al. | |
| 5,059,423 A | 10/1991 | Magruder et al. | |
| 5,112,614 A | 5/1992 | Magruder et al. | |
| 5,137,727 A | 8/1992 | Eckenhoff | |
| 5,176,620 A | 1/1993 | Gilman | |
| 5,193,539 A | 3/1993 | Schulman et al. | |
| 5,193,540 A | 3/1993 | Schulman et al. | |
| 5,215,086 A | 6/1993 | Terry, Jr. et al. | |
| 5,234,692 A | 8/1993 | Magruder et al. | |
| 5,234,693 A | 8/1993 | Magruder et al. | |
| 5,269,303 A | 12/1993 | Wernicke et al. | |
| 5,312,439 A | 5/1994 | Loeb | |
| 5,318,502 A | 6/1994 | Gilman | |
| 5,330,515 A | 7/1994 | Rutecki et al. | |
| 5,540,734 A | 7/1996 | Zabara | |
| 5,575,813 A | 11/1996 | Edell et al. | |
| 5,728,396 A | 3/1998 | Peery et al. | |
| 5,995,873 A | 11/1999 | Rhodes | |
| 6,016,449 A | 1/2000 | Fischell et al. | |
| 6,051,017 A | 4/2000 | Loeb et al. | |
| 6,128,538 A | 10/2000 | Fischell et al. | |
| 6,129,685 A * | 10/2000 | Howard, III | 600/585 |
| 6,161,044 A | 12/2000 | Silverstone | |
| 6,164,284 A | 12/2000 | Schulman et al. | |
| 6,178,349 B1 | 1/2001 | Kieval | |
| 6,185,452 B1 | 2/2001 | Schulman et al. | |
| 6,205,359 B1 | 3/2001 | Boveja | |
| 6,208,894 B1 | 3/2001 | Schulman et al. | |
| 6,248,126 B1 | 6/2001 | Lesser et al. | |
| 6,272,382 B1 | 8/2001 | Faltys et al. | |
| 6,356,788 B2 | 3/2002 | Boveja | |
| 6,358,281 B1 | 3/2002 | Berrang et al. | |
| 6,360,122 B1 | 3/2002 | Fischell et al. | |
| 6,366,814 B1 | 4/2002 | Boveja et al. | |
| 6,368,315 B1 | 4/2002 | Gillis et al. | |
| 6,381,496 B1 | 4/2002 | Meadows et al. | |
| 6,402,678 B1 | 6/2002 | Fischell et al. | |
| 6,402,682 B1 | 6/2002 | Johansson | |
| 6,405,079 B1 | 6/2002 | Ansarinia | |
| 6,415,184 B1 | 7/2002 | Ishikawa et al. | |
| 6,427,086 B1 | 7/2002 | Fischell et al. | |
| 6,450,170 B1 | 9/2002 | Friedman | |
| 6,459,936 B2 | 10/2002 | Fischell et al. | |
| 6,464,687 B1 | 10/2002 | Ishikawa et al. | |
| 6,505,075 B1 | 1/2003 | Weiner | |
| 6,526,318 B1 | 2/2003 | Ansarinia | |
| 6,553,263 B1 | 4/2003 | Meadows et al. | |
| 6,647,296 B2 | 11/2003 | Fischell et al. | |
| 6,648,914 B2 | 11/2003 | Berrang et al. | |
| 6,678,553 B2 | 1/2004 | Lerner et al. | |
| 6,684,105 B2 | 1/2004 | Cohen et al. | |
| 6,721,603 B2 | 4/2004 | Zabara et al. | |
| 6,735,475 B1 | 5/2004 | Whitehurst et al. | |
| 6,760,626 B1 | 7/2004 | Boveja | |
| 6,788,975 B1 | 9/2004 | Whitehurst et al. | |
| 6,882,881 B1 | 4/2005 | Lesser et al. | |
| 6,904,322 B2 | 6/2005 | Katsnelson | |
| 6,978,180 B2 | 12/2005 | Tadlock | |
| 7,526,341 B2 * | 4/2009 | Goetz et al. | 607/45 |
| 2002/0013612 A1 * | 1/2002 | Whitehurst | 607/45 |
| 2002/0019669 A1 | 2/2002 | Berrang et al. | |
| 2002/0198572 A1 | 12/2002 | Weiner | |
| 2003/0004549 A1 | 1/2003 | Hill et al. | |
| 2003/0018368 A1 | 1/2003 | Ansarinia | |
| 2003/0130709 A1 | 7/2003 | D.C. et al. | |
| 2003/0144709 A1 | 7/2003 | Zabara et al. | |
| 2004/0122281 A1 | 6/2004 | Fischell et al. | |
| 2004/0127942 A1 | 7/2004 | Yomtov et al. | |
| 2004/0173221 A1 | 9/2004 | Singhal et al. | |
| 2004/0249429 A1 | 12/2004 | Tadlock | |

FOREIGN PATENT DOCUMENTS

| | | |
|---|---|---|
| WO | WO-82/01656 A1 | 5/1982 |
| WO | WO-94/00185 A1 | 1/1994 |
| WO | WO-94/00189 A1 | 1/1994 |
| WO | WO-98/43700 A1 | 10/1998 |
| WO | WO-98/43701 A1 | 10/1998 |
| WO | WO-02/09811 A1 | 2/2002 |
| WO | WO-03/063959 A1 | 8/2003 |

* cited by examiner

SKULL-MOUNTED ELECTRICAL STIMULATION SYSTEM AND METHOD FOR TREATING PATIENTS

TECHNICAL FIELD

The present invention generally relates to implantable stimulator systems and methods, and more particularly relates to implantable stimulator systems and methods utilizing one or more implantable leads for treating epilepsy, movement disorders, and other indications.

BACKGROUND ART

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts 1-2% of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Epilepsy is often but not always the result of underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy; in Africa, AIDS and its related infections, malaria and meningitis, are common causes; in India, AIDS, neurocysticercosis and tuberculosis, are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is, therefore, suspected that those who do experience such symptomatic seizures are more vulnerable for similar biochemical/neurotransmitter reasons.

Movement disorders are neurologic syndromes characterized by either an excess or a paucity of movement. These disorders affect approximately two million Americans, including over one million suffering from benign essential tremor, and half a million suffering from Parkinson's disease. A substantial percentage of those afflicted with movement disorders experience a significant decrease in quality of life, suffering such problems as incapacitating tremor, limited mobility, bradykinesia (difficulty consciously initiating movement), dysarthria (difficulty with speech), and consequent social isolation. The etiology of many movement disorders, e.g., benign essential tremor, is poorly understood.

For other movement disorders, e.g., Parkinson's disease, the mechanism of the disorder and even the brain cells affected have been identified, but even with optimal medication and physician care the disease may not be reversed and may even continue to progress. Medications that are effective for movement disorders may have significant side effects and may lose their efficacy over time.

Essential Tremor (ET), a.k.a., Benign Essential Tremor, is the most common movement disorder. It is a syndrome characterized by a slowly progressive postural and/or kinetic tremor, usually affecting both upper extremities. The prevalence of ET in the US is estimated at 0.3-5.6% of the general population. A 45-year study of ET in Rochester, Minn. reported an age- and gender-adjusted prevalence (i.e., the percentage of a population that is affected with a particular disease at a given time) of 305.6 per 100,000 and an incidence (i.e., the rate of new cases of a particular disease in a population being studied) of 23.7 per 100,000.

ET affects both sexes equally. The prevalence of ET increases with age. There are bimodal peaks of onset—one in late adolescence to early adulthood and a second peak in older adulthood. The mean age at presentation is 35-45 years. ET usually presents by 65 years of age and virtually always by 70 years. Tremor amplitude slowly increases over time. Tremor frequency decreases with increasing age. An 8-12 Hz tremor is seen in young adults and a 6-8 Hz tremor is seen in the elderly. Although ET is progressive, no association has been found between age of onset and severity of disability.

Mortality rates are not increased in ET. However, disability from ET is common. Significant changes in livelihood and socializing are reported by 85% of individuals with ET, and 15% report being seriously disabled due to ET. Decreased quality of life results from both loss of function and embarrassment. In a study of hereditary ET, 60% did not seek employment; 25% changed jobs or took early retirement; 65% did not dine out; 30% did not attend parties, shop alone, partake of a favorite hobby or sport, or use public transportation; and 20% stopped driving.

DISCLOSURE OF INVENTION

The present invention provides means for chronically stimulating a nerve(s) including the vagus nerve, a branch(es) of the vagus nerve, the trigeminal ganglion or ganglia, trigeminal nerve(s), a branch(es) of the trigeminal nerve(s) (e.g., ophthalmic nerve(s), maxillary nerve(s), and/or mandibular nerve(s)), facial nerve(s), glossopharyngeal nerve(s), or a branch(es) of any of these neural structures with an implantable neurostimulator. The present invention provides systems and methods for applying electrical stimulation to one or more of these nerves or nerve branches via a "skull-mounted" or "head-mounted" device. Electrical stimulation of such targets may provide significant therapeutic benefit in the management of epilepsy, movement disorders, and other indications defined In the detailed description of the invention section of this document.

The treatment provided by the invention is carried out by employing at least one system control unit (SCU). In one preferred form, and SCU comprises an implantable pulse generator (IPG), and external Behind-the-Ear (BTE) unit, and implantable electrode(s). In this embodiment, the SCU is preferably implanted in a surgically-created shallow depression in, above, or near the mastoid area, with one or more electrode leads attached to the SCU extending subcutaneously and along various paths towards the nerve(s) previously mentioned. Preferred systems also include one or more sensors for sensing symptoms or other conditions that may indicate a need for treatment.

The IPG includes a battery that is much larger than a battery of a typical microstimulator, thus extending the time between recharges and consequent explantation procedures. The BTE unit is adapted be situated on the exterior of a patient, near the location where the IPG is imbedded within the mastoid bone. The BTE unit includes circuitry and an coil used to recharge the IPG transcutaneously.

The SCU preferably includes a programmable memory for storing data and/or control stimulation parameters. This allows stimulation and control parameters to be adjusted to levels that are safe and efficacious with minimal discomfort. Electrical stimulation may be controlled independent of any other stimulation or drug infusion system; alternatively, the SCU may be programmed and combined to operate with other electrical and drug stimulation systems to provide therapy to a patient.

According to a preferred embodiment of the invention, the electrodes used for electrical stimulation are arranged as an array on a very thin implantable lead. Alternately, a lead may only include one electrode, or the electrodes may be situated in a wide array for field stimulation of a desired target. The SCU is programmed to produce either monopolar electrical stimulation, e.g., using the SCU case as an indifferent electrode, or to produce bipolar electrical stimulation, e.g., using one of the electrodes of an electrode array as an indifferent electrode. The SCU includes a means of stimulating (a) nerve (s) either intermittently or continuously. Specific stimulation parameters may provide therapeutic advantages for, e.g., various forms of epilepsy, movement disorders, and other indications.

According to an embodiment of the invention, a method of treating patients may include implanting at least one SCU in a shallow recess of the mastoid area of the skull of a patient, wherein the at least one SCU is capable of controlling the delivery of at least one stimulus to at least one nerve affecting epilepsy, movement disorders, or other indications. This method may also include applying at least one stimulus to at least one nerve in order to at least in part alleviate symptoms of epilepsy, movement disorders, or other indications of the patient being treated. The nerves stimulated according to this method may include any of the body, branches, and roots of at least one of the vagus nerves, the trigeminal nerves, the ophthalmic nerves, the maxillary nerves, the mandibular nerves, the facial nerves, the glossopharyngeal nerves, and the trigeminal ganglion or ganglia.

According to an embodiment of the invention, a system for treating a patient includes at least one lead with at least one electrode, and at least one system control unit having a size and shape suitable for implantation in a recess in the mastoid or other area of the skull. The at least one SCU may include electronic circuitry, programmable memory for receiving and storing prescribed stimulation patterns, and a power source for providing power to the electronic circuitry. The electronic circuitry may generates stimulation pulses in accordance with the prescribed stimulation parameters and is operably connected to at least one of the electrodes through which the stimulation pulses may be delivered to issue adjacent to at least one of the electrodes.

Alternately, the SCU used with the present invention may possess one or more of the following properties:

at least one electrode for applying stimulating current to surrounding tissue;

electronic and/or mechanical components encapsulated in a hermetic package made from biocompatible material(s);

an electrical coil inside the package that receives power and/or data by inductive or radio-frequency (RF) coupling to a transmitting coil placed outside the body in a BTE unit, avoiding the need for electrical leads to connect devices to a central implanted or external controller;

means for receiving and/or transmitting signals via telemetry;

means for receiving and/or storing electrical power within the SCU; and a form factor making the SCU implantable in a depression or opening cut in the mastoid area of the skull.

The power source of the SCU is preferably realized using one or more of the following options:

(1) an external BTE power source coupled to the SCU via an RF link;

(2) a self-contained power source made using any means of generation or storage of energy, e.g., a primary battery, a replenishable or rechargeable battery, a capacitor, a supercapacitor; and/or (3) if the self-contained power source is replenishable or rechargeable, a means of replenishing or recharging the power source, e.g., an RF link, an optical link, or other energy-coupling link.

According to one embodiment of the invention, an SCU operates independently. According to another embodiment of the invention, an SCU operates in a coordinated manner with other implanted SCUs, other implanted devices, or with devices external to the patient's body.

According to yet another embodiment of the invention, an SCU incorporates means of sensing epilepsy, movement disorders, and other indications or symptoms thereof, or other measures of the state of the patient. Sensed information is preferably used to control the electrical stimulation parameters of the SCU in a closed-loop manner. According to one embodiment of the invention, the sensing and stimulating means are incorporated into a single SCU. According to another embodiment of the invention, the sensing means communicates sensed information to at least one SCU with stimulating means.

Thus, the present invention provides systems and methods for the treatment of epilepsy, movement disorders, and other indications using at least one SCU. The present invention's advantages include, inter alia: monitoring and programming capabilities; power source, storage, and transfer mechanisms; device activation by the patient or clinician; open- and closed-loop capabilities coupled with sensing a need for and/or response to treatment; simple explantation because the IPG is implanted in the mastoid bone and all leads are directly attached to the IPG; and coordinated use of one or more SCUs.

BRIEF DESCRIPTION OF DRAWINGS

The above and other aspects of the present invention will be more apparent from the following more particular description thereof, presented in conjunction with the following drawings wherein.

Corresponding reference characters indicate corresponding components throughout the several views of the drawings.

MODE(S) FOR CARRYING OUT THE INVENTION

Figure 1A:
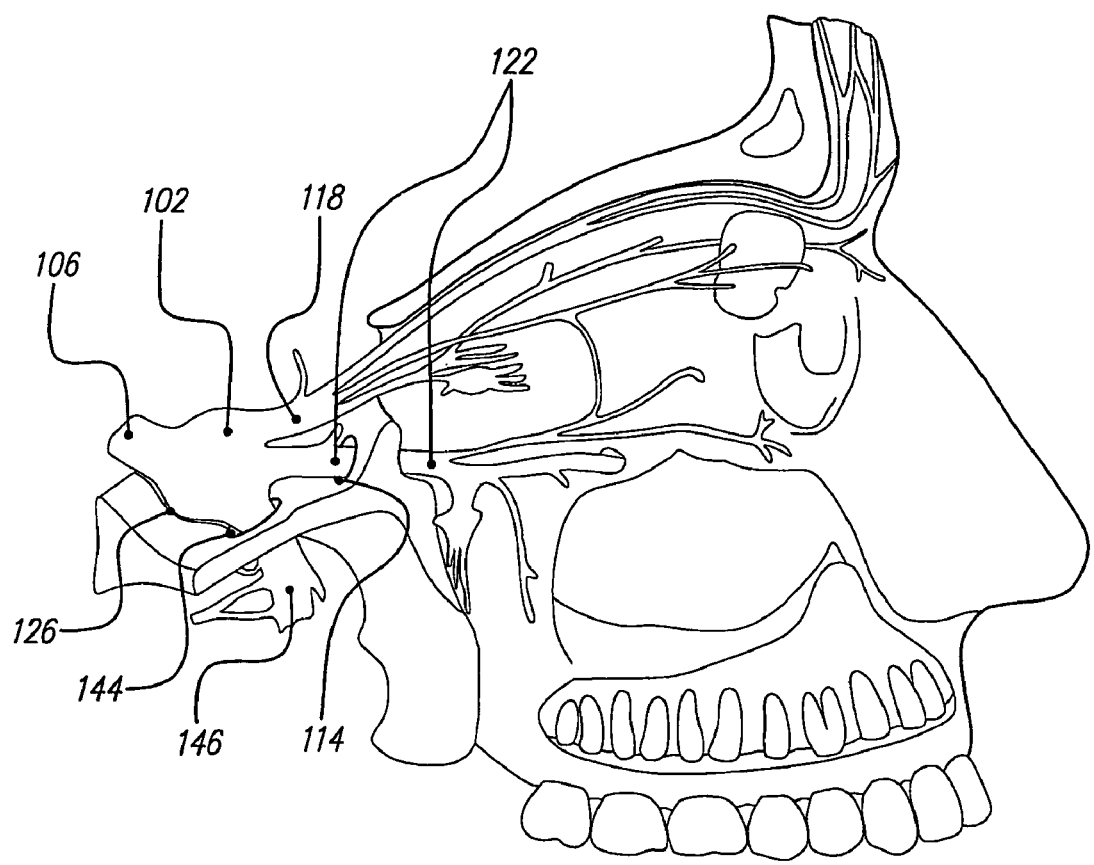
FIG. 1A depicts various nerve branches dorsal to the trigeminal nerve and nearby bony structures.

The following description is of the best mode presently contemplated for carrying out the invention. This description is not to be taken in a limiting sense, but is made merely for the purpose of describing the general principles of the invention. The scope of the invention should be determined with reference to the claims.

Discussed herein are ways to effectively use implantable, chronic neurostimulators for treating, controlling, and/or preventing certain indications including: epilepsy, mood disorders (including depression and bipolar disorder), anxiety disorders (including generalized anxiety disorder and obsessive-compulsive disorder), chronic pain (including visceral pain, neuropathic pain and nociceptive pain), hypertension, cardiac disorders (including tachycardia, bradycardia, other arrhythmias, congestive heart failure, and angina pectoris), psychotic disorders (including schizophrenia), cognitive disorders, dementia (including Alzheimer's disease, Pick's disease, and multi-infarct dementia), sleep disorders (including insomnia, hypersomnia, narcolepsy, and sleep apnea), movement disorders (including Parkinson's disease and essential tremor), and/or headache (including migraine and chronic daily headache). The phrases "epilepsy, movement disorders, and other indications" and "epilepsy, movement disorders, or other indications" as used within each section of this document shall be construed to include the indications listed in the sentence directly preceding this sentence. The symptoms of epilepsy, movement disorders, and other indications may be relieved with stimulation applied to the following nerve(s): the vagus nerve, a branch(es) of the vagus nerve, the trigeminal ganglion or ganglia, the trigeminal nerve(s), a branch(es) of the trigeminal nerve(s) (e.g., the ophthalmic nerve(s), the maxillary nerve(s), and/or the mandibular nerve(s) and their branches), the facial nerve(s), the glossopharyngeal nerve(s), or a branch(es) of any of these neural structures.

Some neurostimulators used to treat epilepsy, movement disorders, and other indications have limited battery supply and are difficult to explant due to their relatively small size. Yet, some patients treated for epilepsy, movement disorders, and other indications require continuous stimulation at a frequency of at least 100 Hz. Such a high frequency of stimulation may quickly deplete the battery supplies of some neurostimulators and thus require frequent recharging and consequent explantation of the neurostimulators within a relatively short period of time, i.e., about three years.

Recent studies in both developed and developing countries have shown that up to 70% of newly diagnosed children and adults with epilepsy can be successfully treated (i.e., complete control of seizures for several years) with anti-epileptic drugs. After two to five years of successful treatment, drugs can be withdrawn in about 70% of children and 60% of adults without the patient experiencing relapses. However, up to 30% of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patents may have a seizure focus in the hippocampi bilaterally. However, both hippocampi cannot be removed without devastating impacts on long-term memory. Other patients may have a seizure focus that lies adjacent to a critical area such as the speech center.

Vagus nerve stimulation (VNS) has been applied with partial success in patients with refractory epilepsy. In this procedure, an implantable pulse generator (IPG) is implanted in the patient's thorax, and an electrode lead is routed from the IPG, over the clavicle, to the left vagus nerve in the neck. Helix-shaped stimulation and indifferent electrodes are attached to the vagus nerve.

The exact mechanism of action of VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," Epilepsia, 1999 August) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, bicuculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. concludes that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nucleus) receives somatic sensory input from all cranial nerves, with much of its input coming from the vagus nerve.

Convincing evidence has been given that a significant number of neurons in the trigeminal nerve project to the NTS. By applying horseradish peroxidase to peripheral branches of the trigeminal nerve in the cat, it was found that branches of the trigeminal nerve (the lingual and pterygopalatine nerves) were found to contain fibers which ended ipsilaterally in the rostral portions of the NTS, massively in the medial and ventrolateral NTS, moderately In the intermediate and interstitial NTS, and sparsely in the ventral NTS. (The rostral-most part of the NTS was free from labeled terminals.) After injecting the enzyme into the NTS portions rostral to the area postrema, small neurons were scattered in the maxillary and mandibular divisions of the trigeminal ganglion. It was concluded that trigeminal primary afferent neurons project directly to the NTS. By staining for substance P immunoreactivity, it was found that Substance P-containing trigeminal sensory neurons project to the NTS.

There is also convincing evidence that a significant number of neurons in the trigeminal nucleus project to the NTS as well. In one study, retrograde transport of a protein-gold complex was used to examine the distribution of spinal cord and trigeminal nucleus caudalis neurons that project to the NTS in the rat. The authors found that retrogradely labeled cells were numerous in the superficial laminae of the trigeminal nucleus caudalis, through its rostrocaudal extent Since the NTS is an important relay for visceral afferents from both the glossopharyngeal and vagus nerves, it is suggested that the spinal and trigeminal neurons that project to the NTS may be part of a larger system that integrates somatic and visceral afferent inputs from wide areas of the body. The projections may underlie somatovisceral and/or visceroviseral reflexes, perhaps with a significant afferent nociceptive component.

Another study utilized microinfusion and retrograde transport of D-[3H]-aspartate to identify excitatory afferents to the NTS. The authors found that the heaviest labeling was localized bilaterally in the trigeminal nucleus with cells extending through its subdivisions and the entire rostrocaudal axis.

In addition, a study by Fanselow, et al. ("Reduction of pentylenetetrazole-induced seizure activity in awake rats by seizure-triggered trigeminal nerve stimulation," Journal of Neuroscience, 2000 November) demonstrated that unilateral stimulation via a chronically implanted nerve cuff electrode applied to the infraorbital branch of the trigeminal nerve led to a reduction in electrographic seizure activity of up to 78%. The authors reported that bilateral trigeminal stimulation was even more effective.

Figure 1B:
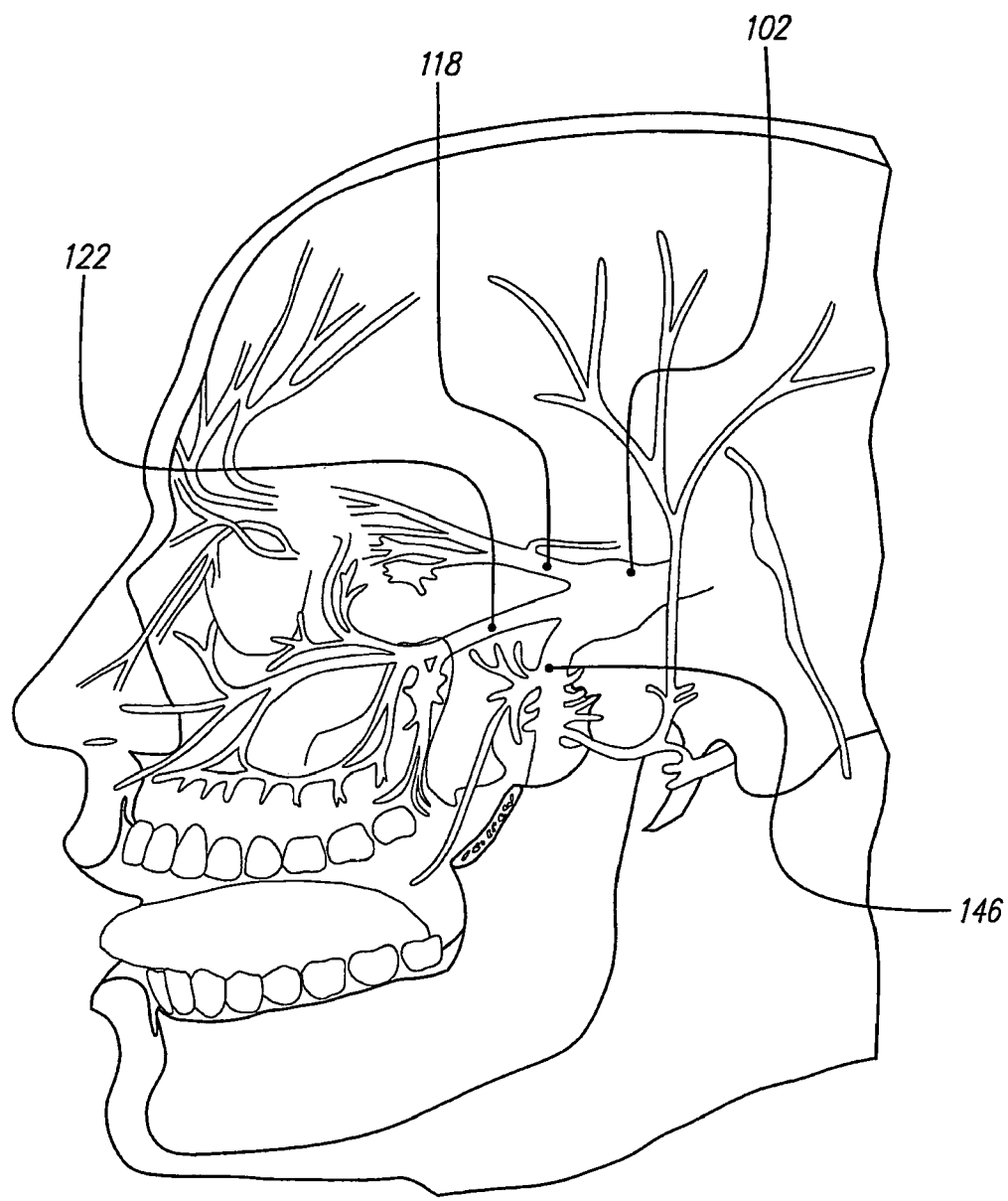
FIG. 1B illustrates the trigeminal nerve, and nerve branches dorsal and proximal to the trigeminal nerve.

FIGS. 1A and 1B depict the trigeminal nerve and its branches. The trigeminal nerve 106 on each side of the head arises from a trigeminal ganglion 102, which lies within the skull in an area known as Meckel's cave 126. In accordance with the teachings of the present invention, access to a trigeminal ganglion 102 may be gained via the foramen ovale 144 or the foramen rotundum 114 in order to implant a lead with at least one electrode adjacent to one or both of the trigeminal ganglia 102. A lead may travel other paths to access the trigeminal ganglion 102 from an IPG implanted in or near the mastoid area of the skull; these other paths will be known to those of skill in the art.

Procedures that ablate the trigeminal ganglia 102 do not disable the muscles of mastication, since the cell bodies of the sensory portion of the nerve are within the trigeminal ganglion, whereas the motor portion simply projects axons through the ganglia (the motor neuron cell bodies are in the pons). This may provide a mechanism for selective stimulation of the sensory cells via appropriate placement of at least one electrode of a lead for stimulation of one or both trigeminal ganglia 102.

The lead of a neurostimulator may additionally or alternatively be implanted adjacent to the trigeminal nerve 106 or any of its branches distal to one or both trigeminal ganglia 102, such as the ophthalmic nerve 118, the maxillary nerve 122, the mandibular nerve 146, and/or branch(es) of any of these. The ophthalmic nerve 118 and the maxillary nerve 122 are entirely sensory, and sufficiently separate to allow independent and selective stimulation via appropriate placement at least one electrodes.

The mandibular nerve 146 is both sensory and motor. The mandibular nerve 146 innervates several facial muscles, including the muscles of mastication and the tensor tympani, which reflexively damps down the vibrations of the malleus by making the tympanic membrane more tense. However, just distal to the foramen ovale 144, the mandibular nerve 146 splits into a purely sensory branch that innervates the superior part of the lower jaw. And slightly more distally, another branch splits into a purely sensory branch that innervates the inferior part of the lower jaw. These branches may be sufficiently separate to allow independent and selective stimulation via appropriate placement of at least one electrode.

Figure 1C:
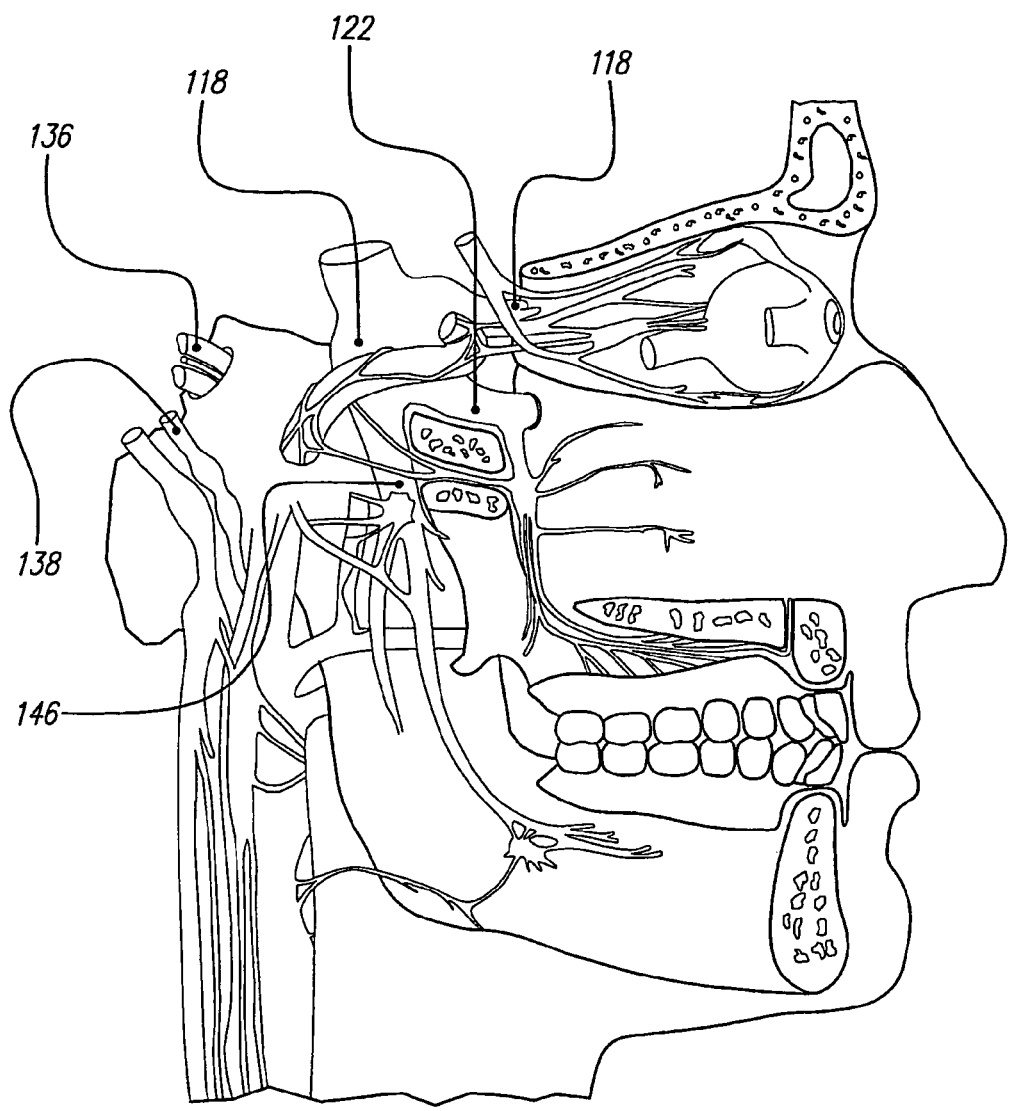
FIG. 1C illustrates various autonomic nerves in the head.

Epilepsy may also be relieved with stimulation additionally or alternatively applied to the facial nerve(s) 136, glossopharyngeal nerve(s) 138, and/or branches of any of these (see FIG. 1C).

In accordance with the teachings of the present invention, electrical stimulation at one or more of the above-mentioned and/or other trigeminal nerve branches is provided to relieve epilepsy. At least one lead with at least one electrode may be implanted adjacent to one or more of the above-identified nerves or nerve structures.

As mentioned above, vagus nerve stimulation (VNS) has demonstrated limited efficacy in the treatment of patients with medically refractory epilepsy. As stated, the mechanism of action of VNS has not been confirmed, but a number researchers believe that VNS may exert its seizure reduction effects through afferent stimulation of the nucleus of tractus solitarius (NTS).

As detailed above, studies have shown that the trigeminal nerve also contributes a significant number of afferent fibers to the NTS. Additionally, trigeminal nerve afferents synapse on the trigeminal nucleus in the brainstem, and afferents from the trigeminal nucleus also project to the NTS. Thus, electrical stimulation of, for example, a trigeminal ganglion, trigeminal nerve, or branch(es) of the trigeminal nerve may reasonably be expected to demonstrate efficacy in the treatment of patients with medically refractory epilepsy.

The trigeminal nerve provides sensory innervation to the face, so stimulation may produce a tingling sensation. However, this feeling has not been reported to be unpleasant in patients undergoing sensory nerve stimulation, and in time, patients grow accustomed to the sensation. The trigeminal nerve also innervates the muscles of mastication, so excessive stimulation of these branches may cause fatigue or even spasm of the mandible (i.e., lockjaw). Stimulation of branches that are distal to the motor fibers of the trigeminal nerve should allow these potential motor side effects to be avoided altogether.

As previously mentioned, vagus nerve stimulation is currently used as a therapy for refractory epilepsy, and studies have suggested that such stimulation may also be an efficacious therapy for tremor, depression, and other indications.

In 2001, Handforth, et al. studied whether vagus nerve stimulation could suppress tremor in the harmaline tremor model in the rat. [See Handforth, et al., "Suppression of harmaline-induced tremor in rats by vagus nerve stimulation" *Movement Disorders* 2001 January; 16(1):84-8.] Animals were chronically implanted with helical leads around the left vagus nerve and a disk-shaped electrode was positioned subcutaneously in the dorsal neck. Harmaline-induced tremor was recorded on a physiograph while each animal received a sequence of five 20-minute trials. Each trial consisted of five minutes of pre-stimulation baseline, five minutes of vagus nerve stimulation, and ten minutes of post-stimulation. Vagus nerve stimulation significantly suppressed harmaline-induced tremor. The suppressive effect was present within the first minute of simulation and was reproducible across the five trials of the study. The results of this study suggest that the central generator or expression of tremor in the harmaline animal model can be suppressed by vagus nerve stimulation. This further suggest that vagus nerve stimulation may be an effective therapy for essential tremor and perhaps for other movement disorders.

Patients suffering from tremor and other symptoms may undergo surgery to lesion a part of the brain, which may afford some relief. However, a lesion is irreversible, and it may lead to side effects such as dysarthria or cognitive disturbances. Additionally, lesions generally yield effects on only one side (the contralateral side), and bilateral lesions are significantly more likely to produce side effects. Other surgical procedures, such as fetal tissue transplants, are costly and unproven.

Figure 1D:
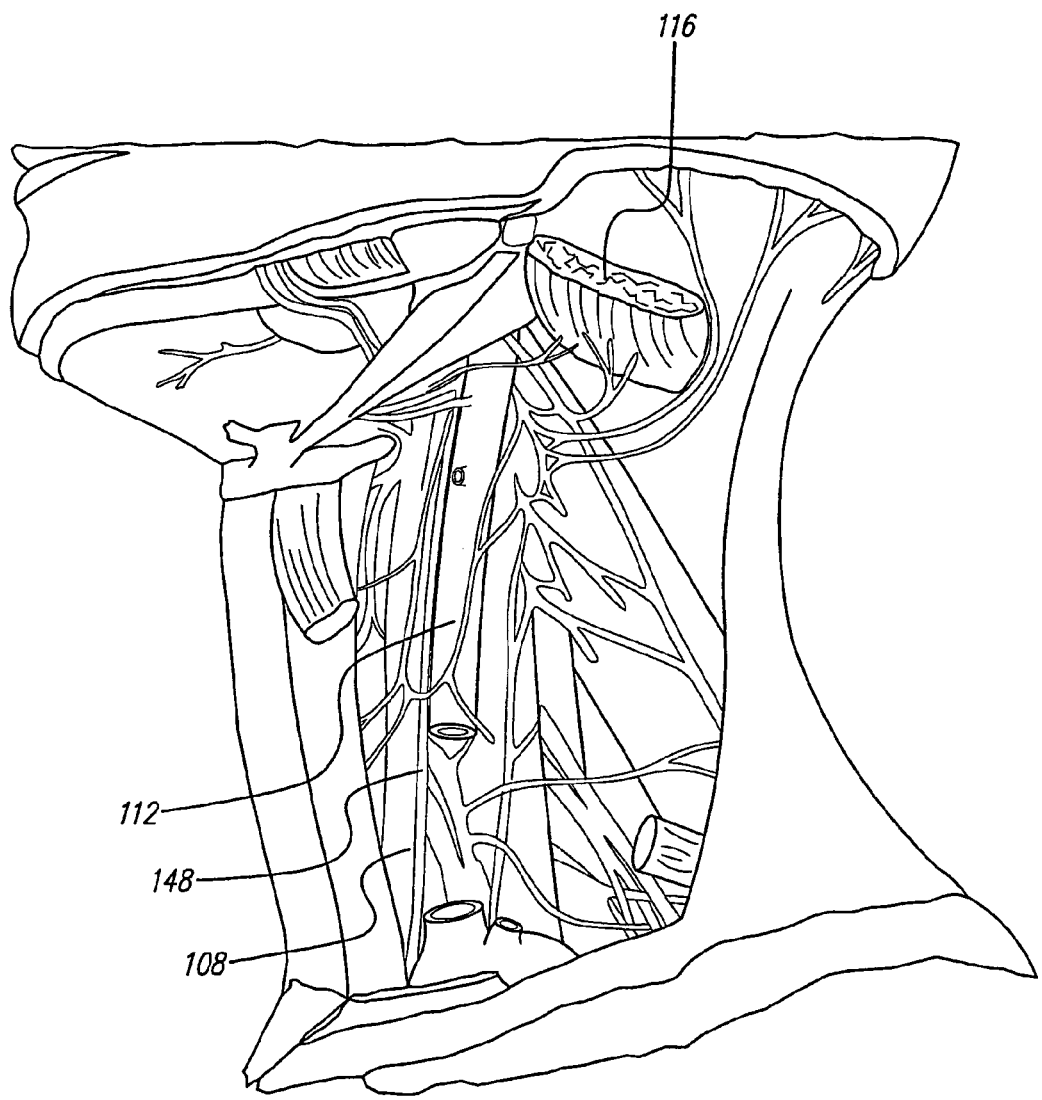
FIG. 1D depicts various nerves, muscles, arteries, and veins in the neck.
Figure 1E:
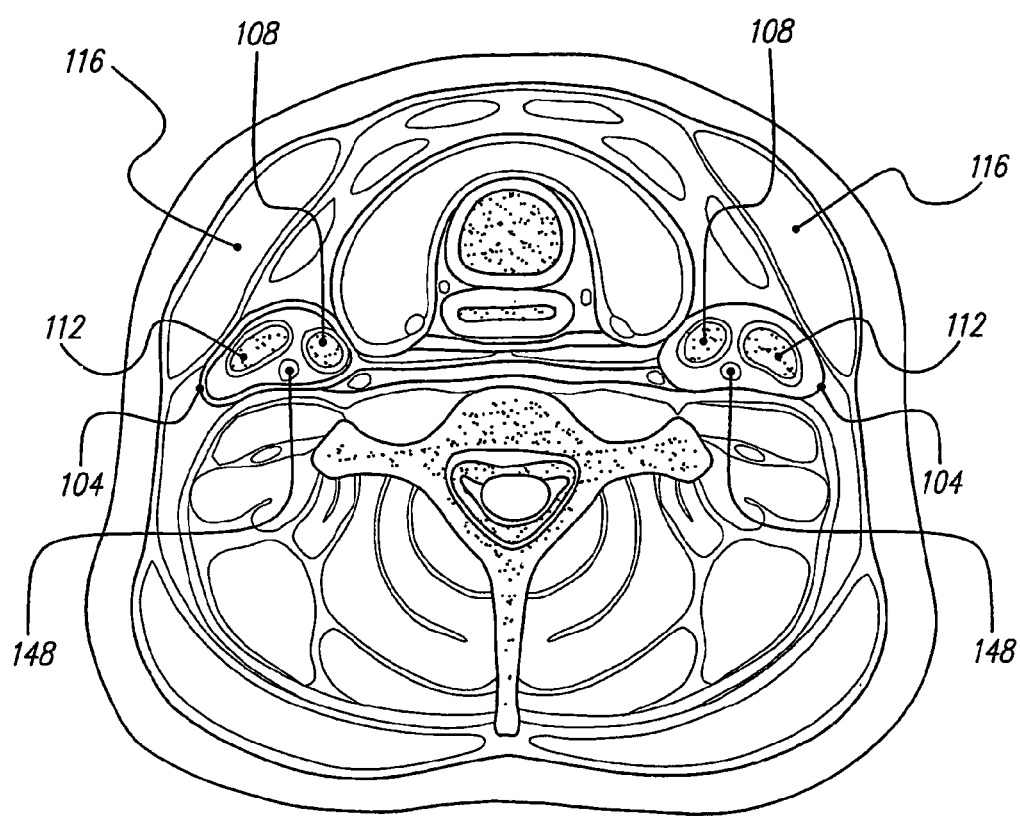
FIG. 1E is a cross-section through the neck, at the level of cervical vertebra C7.

FIG. 1D depicts nerves, muscles, arteries, and veins in the neck, while FIG. 1E is a cross-section through the neck, at the level of cervical vertebra C7. As can be seen, the vagus nerve 148 is relatively easily accessible in the neck. The vagus nerve lies within the carotid sheath 104, along with the common carotid artery 108 and the internal jugular vein 112. The carotid sheath 104 lies beneath the sternocleidomastoid muscle 116, which, in FIG. 1D, is cut and turned up.

Figure 1F:
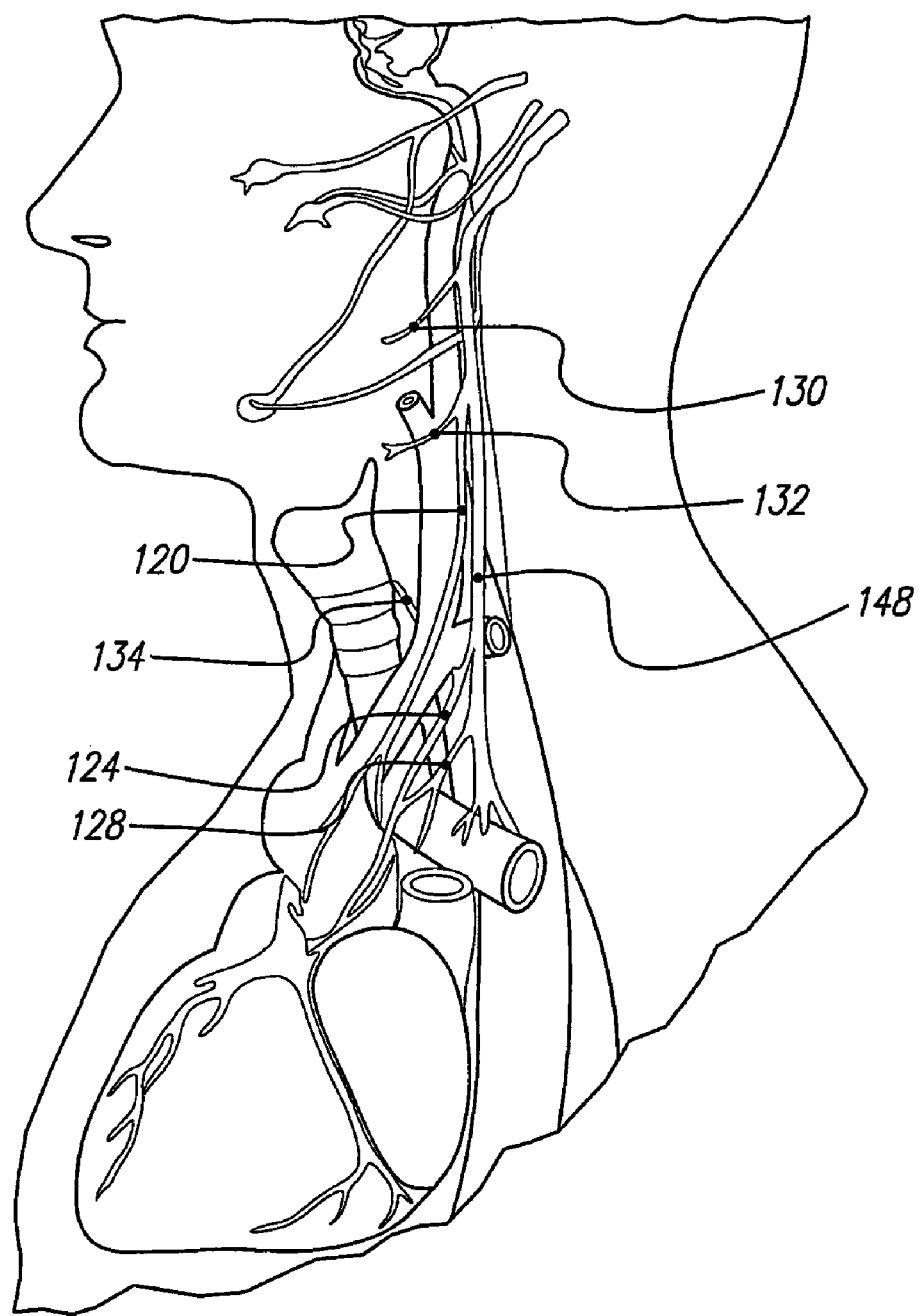
FIG. 1F illustrates various autonomic nerves in the head, neck, and thorax.

FIG. 1F illustrates various autonomic nerves in the head, neck, and thorax. The vagus nerve 148 has a number of nerve branches. Three of these branches are named the superior cervical cardiac branch 120, the inferior cervical cardiac branch 124, and the thoracic cardiac branch 128. Advantageously, these branches are sufficiently separate from the vagus nerve 148 to allow independent and selective stimulation of the vagus nerve 148 and/or its branches via appropriate placement of at least one electrode.

In accordance with the teachings of the present invention and as discussed in more detail presently, electrical stimulation at one or more locations along the vagus nerve 148 and/or its branches is provided to treat, control, and/or prevent epilepsy, mood disorders (including depression and bipolar disorder), anxiety disorders (including generalized anxiety disorder and obsessive-compulsive disorder), chronic pain (including visceral pain, neuropathic pain and nociceptive pain), hypertension, cardiac disorders (including tachycardia, bradycardia, other arrhythmias, congestive heart failure, and angina pectoris), psychotic disorders (including schizophrenia), cognitive disorders, dementia (including Alzheimer's disease, Pick's disease, and multi-infarct dementia), sleep disorders (including insomnia, hypersomnia, narcolepsy, and sleep apnea), movement disorders (including Parkinson's disease and essential tremor), and/or headache (including migraine and chronic daily headache). At least one lead Including at least one electrode may be implanted adjacent the vagus nerve via a relatively complex surgical procedure known in the art.

Stimulation of the vagus nerve may occur distal to (i.e., below) the superior cervical cardiac branch 120, or distal to both the superior cervical cardiac branch 120 and the inferior cervical cardiac branch 124, and may, for instance, be applied to the left vagus nerve. Stimulation of the left vagus nerve distal to the superior cervical cardiac branch 120 and/or the inferior cervical cardiac branch 124 does not pose the cardiac risks that can be associated with vagus nerve stimulation applied proximal to one or both of these nerve branches. Alternatively, some patients may benefit from vagus nerve stimulation applied distal to the thoracic cardiac branch 128.

As used herein, stimulation of the vagus nerve may include stimulation of the vagus nerve and/or one or more of its branches. For instance, to relieve sleep disorders (such as insomnia, hypersomnia, narcolepsy, sleep apnea, and the like), the vagus nerve may be stimulated. More specifically, one or more of the pharyngeal branch of the vagus nerve 130, the superior laryngeal branch of the vagus nerve 132, the pharyngeal plexus (not shown), the left and/or right recurrent laryngeal branch of the vagus nerve 134, and/or other branches of the vagus nerve may be stimulated to relieve sleep disorders.

Figure 2:
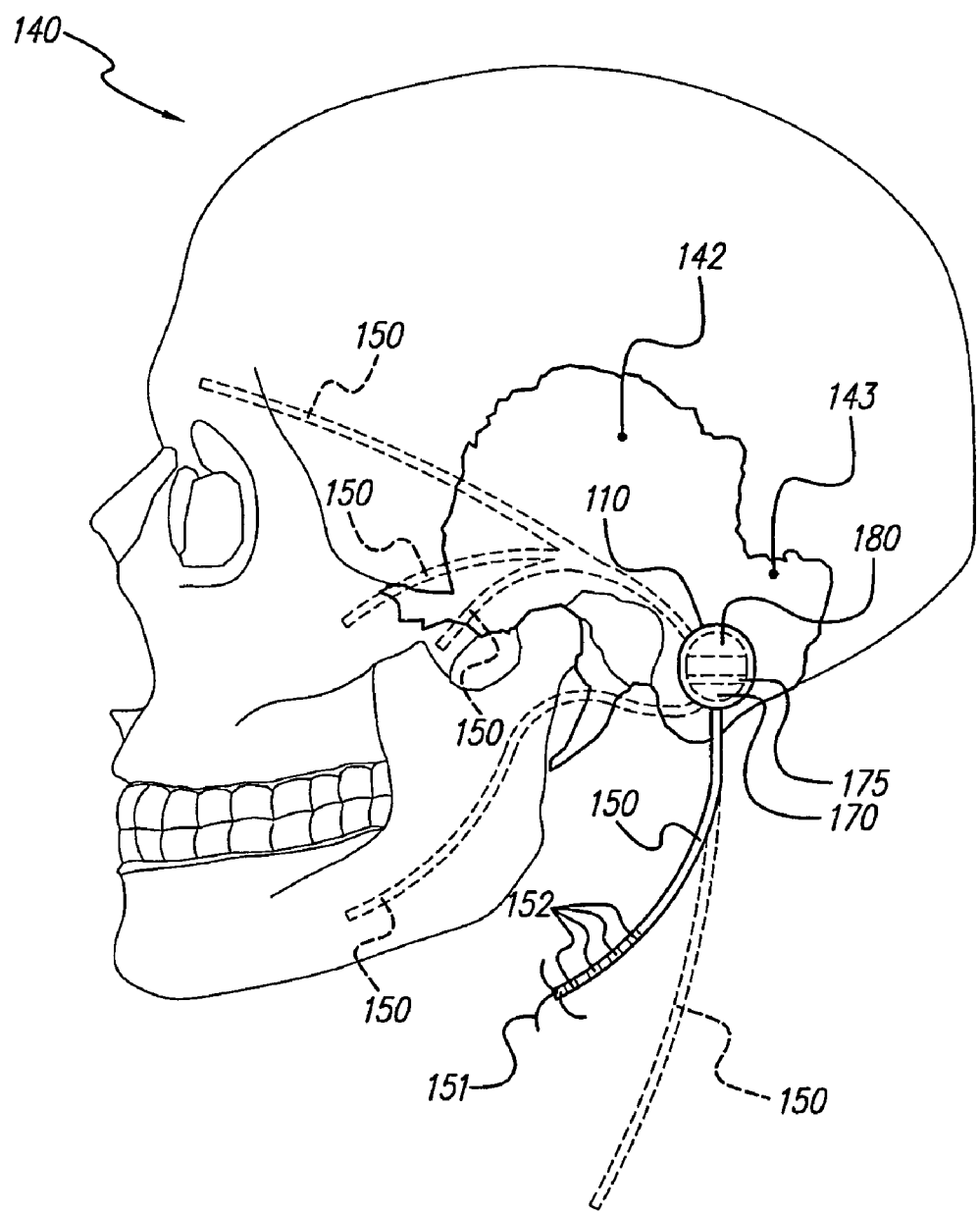
FIG. 2 illustrates a lateral view of the skull.

As depicted in FIG. 2, system control unit (SCU) 110 may be implanted beneath the scalp in a surgically-created shallow depression or opening in the mastoid area 143 of the temporal bone 142 of the skull 140. Alternatively, SCU 110 may be placed on the surface of bone or tissue without bone carving. SCU 110 includes at least an implantable pulse generator (IPG) that is capable of delivering electrical pulse through at least one lead to at least one electrode in order to stimulate tissue. SCU 110 may additionally include structure capable of discharging drugs through at least one catheter to certain tissue. SCU 110 may additionally include a closed loop system with circuitry capable of (1) sensing a condition within the body through at least one lead with at least one sensing electrode and (2) then responding to the sensed condition by modifying stimulation or drug infusion parameters.

SCU 110 preferably conforms to the profile of surrounding tissue(s) and/or bone(s), and is small and compact. This is preferable so that no unnecessary pressure is applied to the skin or scalp, as this may result in skin erosion or infection. SCU 110 preferably has a diameter of no greater than 75 mm, more preferably no greater than 65 mm, and most preferably about 35-55 mm. SCU thickness (e.g., depth into the skull) of approximately 10-12 mm is preferred, while a thickness of about 8-10 mm or less is more preferred.

The method of implanting the SCU 110 of the present invention in the mastoid area 143 of the temporal bone 142 of the skull 140 is superior to prior methods of implanting similar devices in the skull for several reasons. First, the method of the present invention contemplates implantation in the mastoid area 143 because the mastoid area 143 of the temporal bone is relatively thicker than other areas of the skull 140. Second, the method of the present invention of implanting SCU 110 in the mastoid area 143 contemplates Implantation of the SCU 110 in a shallow recession or depression cut into the mastoid area 143 rather than a hole cut entirely through the skull 140. By not cutting a hole through the skull, the method of the present invention maintains maximal integrity of the skull 140 and thereby avoids possible injury and infection that could otherwise accompany an exposure of the fragile tissues of the brain or inner ear. The method of the present invention need not cut a hole through the skull because, as will be shown, lead(s) 150 travel to the trigeminal, vagus, and other nerves (see also FIG. 5) that are located outside the skull (although the present invention may also include a lead or catheter that stimulates, senses, or infuses drugs within the skull in combination with the stimulation or treatment of other tissue located outside the skull). Thus, the present invention is an improvement over prior systems and methods and gracefully avoids unnecessary intracranial intrusions.

As previously mentioned, vagus nerve stimulation (VNS) has been applied with partial success in patients with refractory epilepsy by implanting an IPG in the patient's thorax and routing an electrode lead from the IPG, over the clavicle, to the left vagus nerve in the neck. Unfortunately, routing the lead from the thorax to the neck may cause unwanted movement of the lead during articulation of the joints of the neck. It is believed that implantation of the IPG in the mastoid area of the skull and routing a lead from the skull to the nerves of the neck will result in less movement of the lead during articulation of the joints of the neck. Further, the lead of the present invention will not have to be routed over the clavicle, which routing may cause the lead to be more prone to breaking and shorting out. Further, by routing the lead of th present invention from the mastoid to the nerves in the neck, the lead may be routed along the sternocleidomastoid muscle which naturally travels from the lateral location of the mastoid bone to the medial location of the sternum. The sternocleidomastoid muscle may afford the lead added protection. Finally, implantation of the IPG in the mastoid area of the skull rather than below the clavicle provides optimal placement and ready access to the trigeminal and other facial nerves and to the tissue of the brain, as mentioned previously. The mastoid bone, or surrounding areas, provides a more central location for orchestrated stimulating, sensing, and drug infusing of various nerves and muscles of the head and neck, than a location below the clavicle, such as the patient's thorax. Thus, the present invention is an improvement over a system employing an IPG implanted in the thorax.

One or more electrode lead(s) 150 attached to SCU 110 run subcutaneously, preferably in a surgically-created (a) shallow recess(es) or groove(s) in the mastoid area 143 of the skull 140, to the nerves of FIGS. 1A-1F. Shallowly-recessed placement of the SCU 110 and the lead(s) 150 has the advantages of decreased likelihood of erosion of the overlying skin, and of minimal cosmetic impact. The mastoid area 143 of the temporal bone 142 is a particularly advantageous location to recess the SCU 110 and the lead(s) 150 because the mastoid process is relatively thick in relation to the rest of the bones of the skull.

At least one, and preferably one to four, electrode(s) 152 are carried on lead(s) 150 having a proximal end coupled to SCU 110. The lead contains wires electrically connecting electrodes 152 to SCU 110. SCU 110 contains electrical components 170 that produce electrical stimulation pulses that travel through the wires of lead(s) 150 and are delivered to electrodes 152, and thus to the neural tissue that surrounds electrodes 152. To protect the electrical components inside SCU 110, the case of the SCU 110 is preferably hermetically sealed. For additional protection against, e.g. impact, the case is preferably made of metal (e.g. titanium), silastic, or ceramic, which materials are also, advantageously, biocompatible. In addition, SCU 110 is preferably Magnetic Resonance Imaging (MRI) compatible.

Lead(s) 150, and any other leads of the present invention, may include tines, barbs, or other means of anchoring 151 (see FIG. 2) the electrode(s) on such leads in, or near, the following nerve(s): the vagus nerve, a branch(es) of the vagus nerve, the trigeminal ganglion or ganglia, the trigeminal nerve(s), a branch(es) of the trigeminal nerve(s) (e.g., the ophthalmic nerve(s), the maxillary nerve(s), and/or the mandibular nerve(s)), the facial nerve(s), the glossopharyngeal nerve(s), or a branch(es) of any of these neural structures. The lead(s) of the present invention are tunneled under the skin to the implantable pulse generator of the SCU 110 where it/they attach to the implantable pulse generator via a connector. A suture sleeve or other fixation device may be placed at any point along the lead(s) to hold it/them in place.

In one embodiment of the present invention, the electrical stimulation may be provided as described in U.S. Patent Application Publication No. 2002/0161403 (the '403 application), filed under the Patent Cooperation Treaty on Jan. 12, 2001 as International Patent Application No. PCT/US01/04417 (which claims priority to U.S. Provisional Patent Application Ser. No. 60/182,486, filed Feb. 15, 2000). As such, the electrical stimulation of the present invention may be as provided in this application, which is directed to a "Deep Brain Stimulation System for the Treatment of Parkinson's Disease or Other Disorders".

The present invention may include one or more SCUs to deliver electrical stimulation and/or drug infusion to a patient. These SCUs may include an SCU with an IPG, i.e., as illustrated in FIG. 2; a microstimulator SCU, such as a BION® microstimulator of Advanced Bionics Corporation (Valencia, Calif.); or an SCU with an implantable drug infusion pump. When needed, an SCU provides both electrical stimulation and one or more stimulating drugs. Each of these SCUs may work in communication with each other to provide therapy to a patient at or near the following nerve(s): the vagus nerve, a branch(es) of the vagus nerve, the trigeminal ganglion or ganglia, the trigeminal nerve(s), a branch(es) of the trigeminal nerve(s) (e.g., the ophthalmic nerve(s), the maxillary nerve(s), and/or the mandibular nerve(s)), the facial nerve(s), the glossopharyngeal nerve(s), or a branch(es) of any of these neural structures.

Any one SCU may contain multiple stimulating leads, sensory leads, and/or catheters in order to simultaneously, and/or in concert, stimulate multiple nerves, sense conditions at multiple locates, and/or infuse drugs at to multiple tissue sites. For example, a single SCU may contain two stimulating leads that split to stimulate the trigeminal nerve bilaterally.

SCU 110 preferably contains electronic circuitry 170 for receiving data and/or power from outside the body by inductive, radio-frequency (RF), or other electromagnetic coupling. In a preferred embodiment, electronic circuitry 170 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 110 also advantageously includes programmable memory 175 for storing a set(s) of data, stimulation, and control parameters. This feature allows electrical stimulation to be adjusted to settings that are safe and efficacious with minimal discomfort for each individual. Specific parameters may provide therapeutic advantages for various levels and types of epilepsy, movement disorders, and other indications previously defined in this document. For instance, some patients may respond favorably to intermittent stimulation, while others may require continuous treatment for relief. Electrical stimulation parameters are preferably controlled independently. However, in some instances, they are advantageously coupled with the operations of other SCUs, e.g., electrical stimulation of SCU 110 may be programmed to occur only during drug infusion of another SCU.

In addition, parameters may be chosen to target specific neural populations and to exclude others, or to increase neural activity in specific neural populations and to decrease neural activity in others. For example, excitatory neurostimulation of relatively low frequency (e.g., less than about 50-100 Hz) typically results in activation of surrounding neural tissue and increased neural activity ("excitatory stimulation"), whereas inhibitory stimulation of relatively high frequency (e.g., greater than about 50-100 Hz) typically results in decreased neural activity ("inhibitory stimulation").

The preferred SCU 110 also includes a power source and/or power storage device 180. Possible power options for a stimulation device of the present invention, described in more detail below, include but are not limited to an external power source In a Behind-the-Ear (BTE) unit coupled to the stimulation device, e.g., via: an RF link; a self-contained power source utilizing any means of generation or storage of energy (e.g., a primary battery, a rechargeable battery such as a lithium ion battery, an electrolytic capacitor, or a super- or ultra-capacitor); and, if the self-contained power source is replenishable or rechargeable, means of replenishing or recharging the power source (e.g., an RF link).

Figure 3:
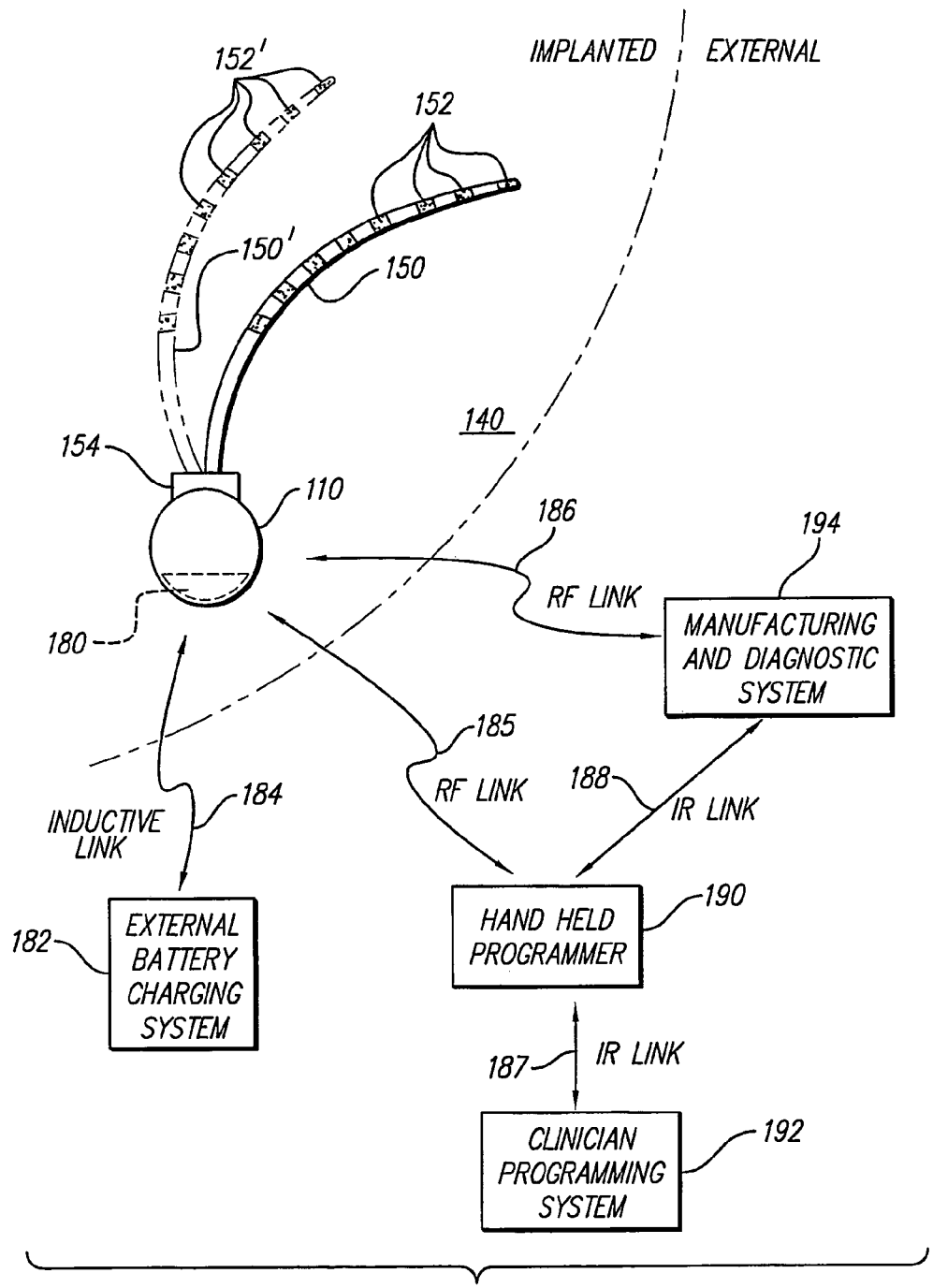
FIG. 3 illustrates internal and external components of an embodiment of the invention.

In one embodiment of the present invention shown in FIG. 3, SCU 110 includes a rechargeable battery as a power source/storage device 180. The battery is recharged, as required, from an external battery charging system (EBCS) 182, typically through an inductive link 184. In this embodiment, and as explained more fully in the earlier referenced '403 application, SCU 110 includes a processor and other electronic circuitry 170 that allow it to generate stimulation pulses that are applied to the patient through electrodes 152 in accordance with a program and stimulation parameters stored in programmable memory 175.

According to an embodiment of the present invention, such as described in the previously referenced '403 application and as depicted in FIG. 3, at least one lead 150 is attached to SCU 110, via a suitable connector 154. Each lead includes at least one electrode(s) 152, preferably one to four electrode(s), and may include as many as sixteen or more electrodes 152. Additional leads 150' may be attached to SCU 110. Hence, FIG. 3 shows (in phantom lines) a second lead 150' having electrodes 152' thereon, also attached to SCU 110.

Lead(s) 150 are preferably less than 5 mm in diameter, and more preferably less than 1.5 mm in diameter. Electrodes 152, 152' are preferably arranged as an array, for example, at least two collinear electrodes or at least 4 collinear electrodes. SCU 110 is preferably programmable to produce either monopolar electrical stimulation, e.g., using the SCU case as an indifferent electrode, or bipolar electrical stimulation, e.g., using one of the electrodes of the electrode array as an indifferent electrode. An SCU 110 may have at least four channels and drives up to sixteen electrodes or more.

According to one embodiment of the invention, an SCU operates independently. According to another embodiment of the invention, an SCU operates in a coordinated manner with other SCU(s), other implanted device(s), or other device(s) external to the patient's body. For instance, an SCU may control or operate under the control of another implanted SCU(s), other implanted device(s), or other device(s) external to the patient's body. An SCU may communicate with other implanted SCUs (as mentioned earlier), other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that is preferably capable of receiving commands and/or data from an SCU.

For example, SCU 110 of the present invention may be activated and deactivated, programmed and tested through a hand held programmer (HHP) 190 (which may also be referred to as a patient programmer and is preferably, but not necessarily, hand held), a clinician programming system (CPS) 192 (which may also be hand held), or a manufacturing and diagnostic system (MDS) 194 (which may also be hand held). HHP 190 may be coupled to SCU 110 via an RF link 185. Similarly, MDS 194 may be coupled to SCU 110 via another RF link 186. In a like manner, CPS 192 may be coupled to HHP 190 via an infra-red link 187; and MDS 194 may be coupled to HHP 190 via another infra-red link 188. Other types of telecommunicative links, other than RF or infra-red may also be used for this purpose. Through these links, CPS 192, for example, may be coupled through HHP 190 to SCU 110 for programming or diagnostic purposes. MDS 194 may also be coupled to SCU 110, either directly through RF link 186, or indirectly through the IR link 188, HHP 190, and RF link 185.

Figure 4:
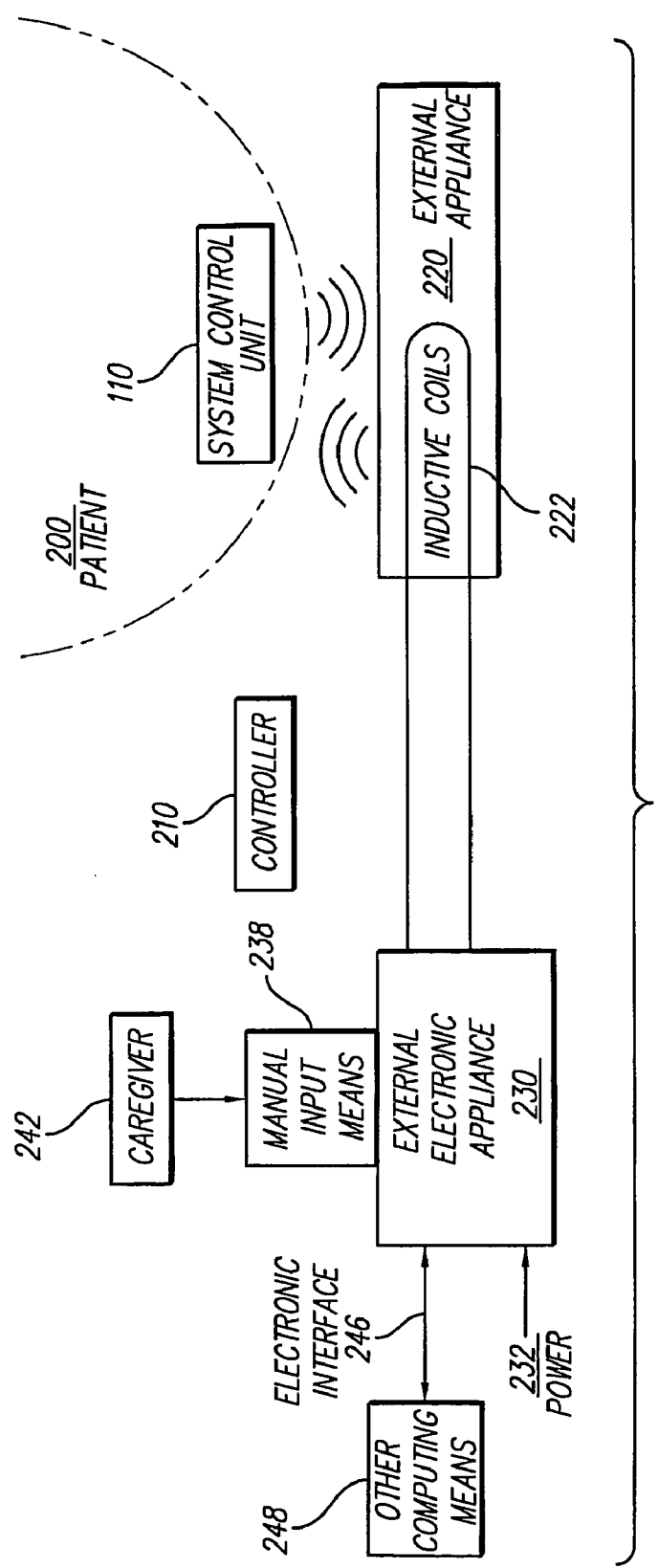
FIG. 4 illustrates external components of an embodiment of the invention.

In another embodiment as illustrated in FIG. 4, the patient 200 switches SCU 110 on and off by use of controller 210, which is preferably hand held. Controller 210 operates to control SCU 110 by any of various means, including sensing the proximity of a permanent magnet located in controller 210, or sensing RF transmissions from controller 210.

External components for one preferred embodiment related to programming and providing power to SCU 110 are also illustrated in FIG. 4. When it is required to communicate with SCU 110, patient 200 is positioned on or near external appliance 220, which appliance contains one or more inductive coils 222 or other means of communication (e.g., RF transmitter and receiver). External appliance 220 is connected to or is a part of external electronic circuitry appliance 230 which receives power 232 from a conventional power source. External appliance 230 contains manual input means 238, e.g., a keypad, whereby the patient 200 or a caregiver 242 may request changes in the parameters of the electrical and/or drug stimulation produced during the normal operation of SCU 110. In this preferred embodiment, manual input means 238 includes various electro-mechanical switches and visual display devices that provide the patient and/or care giver with information about the status and prior programming of SCU 110.

Alternatively or additionally, external electronic appliance 230 is provided with an electronic interface means 246 for interacting with other computing means 248, such as by a serial interface cable or infrared link to a personal computer or to a telephone modem. Such interface means 246 thus permits a clinician to monitor the status of the implant and prescribe new stimulation parameters from a remote location.

The external appliance(s) may advantageously be embedded in a cushion, pillow, hat, or the like. Other possibilities exist, including a head band, patch, or other structure(s) that may be affixed to the patient's body or clothing. External appliances may include a package that can be, e.g., worn on the belt, may include an extension to a transmission coil affixed, e.g., with a Velcro® band or an adhesive, or may be combinations of these or other structures able to perform the functions described herein.

Figure 5:
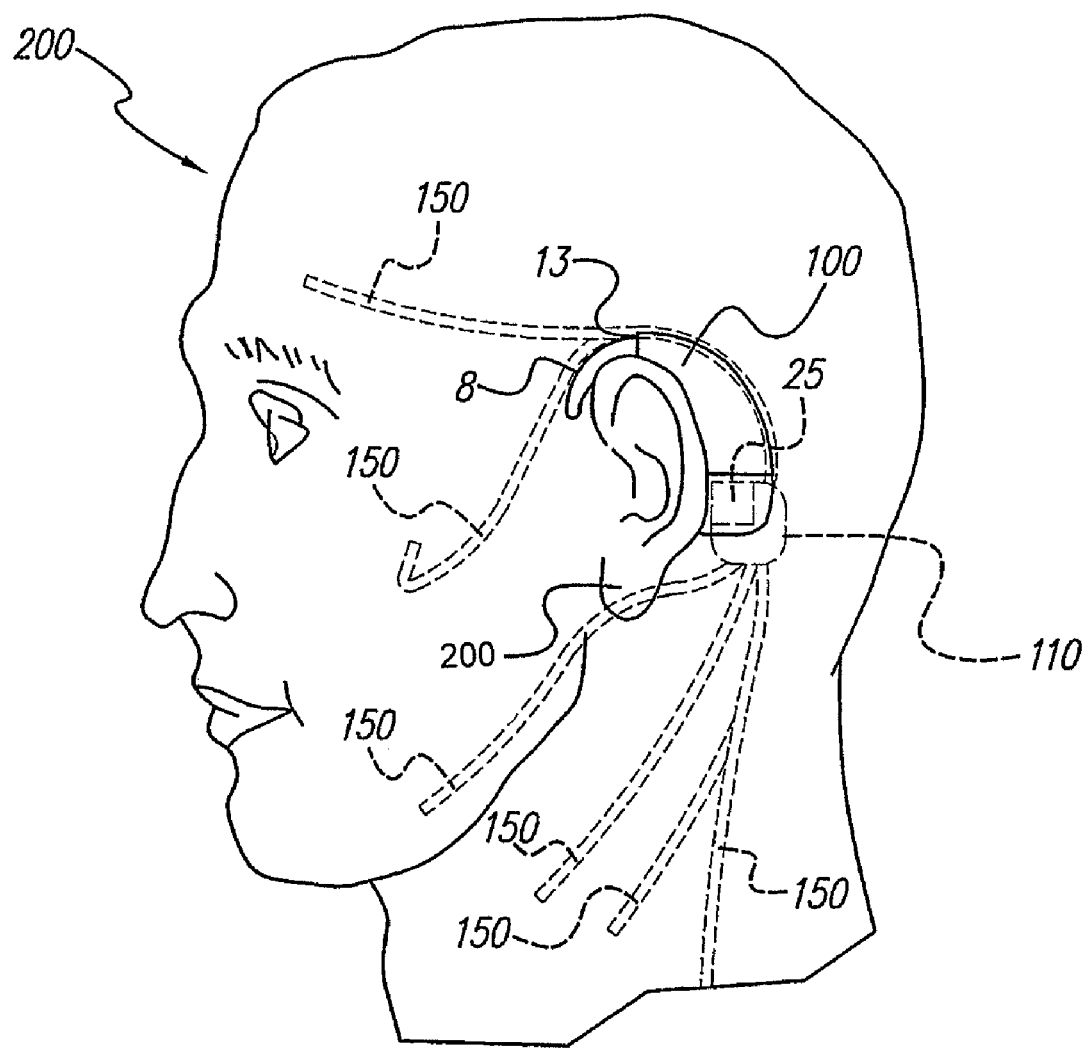
FIG. 5 illustrates a Behind-the-Ear (BTE) unit for use with an embodiment of the invention.

FIG. 5 shows, for example, a Behind-the-Ear (BTE) unit 100 behind the ear of the patient 200. The BTE unit 100 may be attached 13 to an earhook 8 that secures the BTE unit 100 around the auricle of the ear. Additionally, the BTE unit 100 may include a magnet and/or metal plate 25 that is attracted to a corresponding magnet and/or metal plate in the SCU 110. This magnet and/or metal plate helps secure the external BTE unit to the internal SCU 110 so that the two devices maintain communication.

The BTE unit 100 is a preferred example of an external appliance 220 that includes electronic circuitry, a power source, and at least one RF coil, or other means of communicating with the SCU 110 as previously described. Purposes of the BTE unit 100 may include: providing power to the SCU 110; controlling, modifying, or monitoring the activities and/or parameters of the SCU 110; and/or providing a communications transfer to another external appliance, such as external appliance 230.

In the case where the SCU 110 is located in an area of the mastoid bone 143 such that communication between the SCU 110 and the BTE unit 100 is not practical or possible, the BTE unit 100 may alternately be in communication with a head piece that magnetically attracts to the SCU 110. The head piece includes all the components necessary to communicate with the SCU 110 In a manner that is either independent of or supported by the BTE unit 100. For example, the head piece includes at least an RF coil, or other means of communication, and related circuitry necessary to put the head piece in communication with the SCU 110.

In order to help determine the strength and/or duration of electrical stimulation required to produce the desired effect, in one preferred embodiment, a patient's response to and/or need for treatment is sensed. For example, the present invention may include an SCU that senses and measures the electrical activity of a neural population (e.g., EEG) or other relevant activities and substances that will be evident to those of skill in the art upon review of the present disclosure. The sensed and measured information is preferably used to control the stimulation parameters of the SCU(s) in a closed-loop manner.

While an SCU 110 may also incorporate means of sensing activity and/or substances, it may alternatively or additionally be desirable to use a separate or specialized implantable device to record and telemeter physiological conditions/responses in order to adjust electrical stimulation parameters. This information may be transmitted to an external device, such as external appliance 220, or may be transmitted directly to implanted SCU(s) 110. However, in some cases, it may not be necessary or desired to include a sensing function or device, in which case stimulation parameters are determined and refined, for instance, by patient feedback.

Thus, it is seen that in accordance with the present invention, one or more external appliances are preferably provided to interact with SCU 110 to accomplish one or more of the following functions:

Function 1: If necessary, transmit electrical power from the external electronic appliance 230 via appliance 220 to SCU 110 in order to power the device and/or recharge the power source/storage device 180. External electronic appliance 230 may include an automatic algorithm that adjusts electrical stimulation parameters automatically whenever the SCU(s) 110 is/are recharged.

Function 2: Transmit data from the external appliance 230 via the external appliance 220 to SCU 110 in order to change the parameters of electrical and/or drug stimulation produced by SCU 110.

Function 3: Transmit sensed data indicating a need for treatment or in response to stimulation from SCU 110 (e.g., impedance, electrical activity of a neural population (e.g., EEG), or other activity or substances) to external appliance 230 via external appliance 220.

Function 4: Transmit data indicating state of the SCU 110 (e.g., battery level, drug level, electrical stimulation and/or infusion settings, etc.) to external appliance 230 via external appliance 220.

By way of example, a treatment modality for epilepsy, movement disorders, or other indications previously defined in this document is carried out according to the following sequence of procedures:

1. An SCU 110 is implanted so that its electrodes 152 are located adjacent to at least one of the following nerve(s): the vagus nerve, a branch(es) of the vagus nerve, the trigeminal ganglion or ganglia, the trigeminal nerve(s), a branch(es) of the trigeminal nerve(s) (e.g., the ophthalmic nerve(s), the maxillary nerve(s), and/or the mandibular nerve(s)), the facial nerve(s), the glossopharyngeal nerve(s), or a branch(es) of any of these neural structures. If necessary or desired, electrodes 152' may additionally or alternatively be located in or near these or other adjacent nerves.

2. Using Function 2 described above (i.e., transmitting data) of external electronic appliance 230 and external appliance 220, SCU 110 is commanded to produce a series of excitatory electrical stimulation pulses, possibly with gradually increasing amplitude.

3. Set stimulator on/off period to an appropriate setting, e.g., continuously on.

4. After each stimulation pulse, or at some other predefined interval, any change in electrical or other activity of a neural population (e.g., EEG) resulting from the electrical stimulation is sensed, preferably by one or more electrodes 152 and/or 152'. These responses are converted to data and telemetered out to external electronic appliance 230 via Function 3.

5. From the response data received at external appliance 230 from SCU 110, the stimulus threshold for obtaining a response Is determined and is used by a clinician 242 acting directly 238 or by other computing means 248 to transmit the desired electrical parameters to SCU 110 in accordance with Function 2. Alternatively, external appliance 230 makes the proper adjustments automatically, and transmits the proper stimulation parameters to SCU 110. In yet another alternative, SCU 110 adjusts stimulation parameters automatically based on the sensed response.

6. When patient 200 desires to invoke electrical stimulation, patient 200 employs controller 210 to set SCU 110 in a state where it delivers a clinician 242 prescribed stimulation pattern from a predetermined range of allowable stimulation patterns.

7. To cease electrical stimulation, patient 200 employs controller 210 to turn off SCU 110.

8. Periodically, the patient or caregiver recharges the power source/storage device 180 of SCU 110, if necessary, in accordance with Function 1 described above (i.e., transmit electrical power).

For the treatment of any of the various types and levels of epilepsy, movement disorders, and other indications previously defined in this document, it may be desirable to modify or adjust the algorithmic functions performed by the implanted and/or external components, as well as the surgical approaches, in ways that would be obvious and/or advantageous to skilled practitioners of these arts. For example, it may be desirable to employ more than one SCU 110, each of which could be separately controlled by means of a digital address. Multiple channels and/or multiple patterns of electrical and/or drug stimulation might thereby be programmed by the clinician and controlled by the patient in order to deal with complex or multiple symptoms or dysfunctions, such as severe or complex cases of epilepsy, movement disorders, or other indications previously defined in this document.

In one embodiment, SCU 110, or a group of two or more SCUs, is controlled via closed-loop operation. A need for and/or response to stimulation is sensed via SCU 110, or by an additional SCU (which may or may not be dedicated to the sensing function), or by another implanted or external device. If necessary, the sensed information is transmitted to SCU 110. Preferably, the parameters used by SCU 110 are automatically adjusted based on the sensed information. Thus, the electrical and/or drug stimulation parameters are adjusted in a closed-loop manner to provide stimulation tailored to the need for and/or response to the electrical and/or drug stimulation.

In another embodiment, sensing means described earlier may be used to orchestrate first the activation of SCU(s) targeting one or more of the nerves disclosed herein, and then, when appropriate, the SCU(s) targeting another area and/or by a different means. Alternatively, this orchestration may be programmed and not based on a sensed condition.

Thus, the present invention provides systems and methods for the treatment, control, and/or prevention of epilepsy, movement disorders, and other indications previously defined in this document using at least one SCU. The present invention's advantages include, inter alia: monitoring and programming capabilities; power source, storage, and transfer mechanisms; device activation by the patient or clinician; open- and closed-loop capabilities coupled with sensing a need for and/or response to treatment; simple explantation because the IPG is implanted in the mastoid bone and all leads are directly attached to the IPG; and coordinated use of one or more SCUs.

While the invention herein disclosed has been described by means of specific embodiments and applications thereof, numerous modifications and variations could be made thereto by those skilled in the art without departing from the scope of the invention set forth in the claims.

What is claimed is:

1. A method of treating patients with epilepsy, comprising:
   implanting at least one system control unit in a shallow recess of the mastoid area of the skull of a patient; and
   applying at least one stimulus generated by the system control unit to at least one nerve, thereby at least in part alleviating the symptoms of the epilepsy;
   wherein the at least one nerve is selected from at least one of the body, branches, and roots of at least one of the vagus nerves, the trigeminal nerves, the ophthalmic nerves, the maxillary nerves, the mandibular nerves, the facial nerves, the glossopharyngeal nerves, and the trigeminal ganglion or ganglia.

2. The method of claim 1 wherein the system control unit is connected to at least one electrode, and wherein the stimulus comprises electrical stimulation deliverable via the at least one electrode.

3. The method of claim 2 wherein the electrical stimulation is excitatory stimulation.

4. The method of claim 2 wherein the electrical stimulation is inhibitory stimulation.

5. The method of claim 1 further comprising sensing at least one condition and using the at least one sensed condition to automatically determine the stimulus to apply.

6. The method of claim 1 wherein the system control unit is connected to at least one catheter, and wherein the stimulus comprises drug infusion deliverable via the at least one catheter.

7. The method of claim 1, wherein the at least one nerve is at least one of the body, branches, and roots of the vagus nerves.

8. The method of claim 1, wherein the at least one nerve is at least one of the body, branches, and roots of the trigeminal nerves.

9. The method of claim 1, wherein the at least one nerve is at least one of the body, branches, and roots of the ophthalmic nerves.

10. The method of claim 1, wherein the at least one nerve is at least one of the body, branches, and roots of the maxillary nerves.

11. The method of claim 1, wherein the at least one nerve is at least one of the body, branches, and roots of the mandibular nerves.

12. The method of claim 1, wherein the at least one nerve is at least one of the body, branches, and roots of the facial nerves.

13. The method of claim 1, wherein the at least one nerve is at least one of the body, branches, and roots of the glossopharyngeal nerves.

14. The method of claim 1, wherein the at least one nerve is at least one of the body, branches, and roots of and the trigeminal ganglion or ganglia.

* * * * *